United States Patent [19]
Hegar

[11] 3,994,906
[45] Nov. 30, 1976

[54] 3-SULPHOALKYL-6-HYDROXY-PYRID-(2)-ONES

[75] Inventor: Gert Hegar, Schoenenbuch, Switzerland

[73] Assignee: Ciba-Geigy AG, Basel, Switzerland

[22] Filed: June 26, 1975

[21] Appl. No.: 590,784

Related U.S. Application Data

[63] Continuation of Ser. No. 395,812, Sept. 10, 1973, abandoned, which is a continuation of Ser. No. 208,411, Dec. 15, 1971, abandoned.

[30] Foreign Application Priority Data

Dec. 22, 1970 Switzerland.................. 18958/70
Feb. 9, 1971 Switzerland.................. 1873/71
Nov. 23, 1971 Switzerland.................. 17056/71

[52] U.S. Cl.................. 260/294.8 R; 260/156; 260/294.8 F; 8/41 R
[51] Int. Cl.².................. C07D 213/52
[58] Field of Search.............. 260/294.8 R, 294.8 F

[56] References Cited
UNITED STATES PATENTS 3,867,392 2/1975 Heinrich et al............. 260/294.8 R

*Primary Examiner*—Alan L. Rotman
*Attorney, Agent, or Firm*—Joseph G. Kolodny; Edward McC. Roberts; Prabodh I. Almaula

[57] ABSTRACT

A compound of the formula

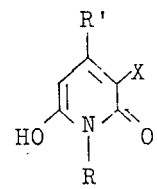

wherein R and R' each represent a hydrogen atom, an alkyl or aryl radical or a heterocyclic radical and X represents a sulphoalkyl group. These compounds are useful as coupling components for the manufacture of dyestuffs which are distinguished by high tinctorial strength.

11 Claims, No Drawings

3-SULPHOALKYL-6-HYDROXY-PYRID-(2)-ONES

This is a continuation of application Ser. No. 395,812, filed Sept. 10, 1973 (now abandoned) which is a continuation of application Ser. No. 208,411 filed on Dec. 15, 1971 (now abandoned).

The invention relates to sulphoalkyl-6-hydroxypyrid-(2)-ones, in particular those that contain a sulphoalkyl group in the 3-position of the pyridone ring. Of the compounds according to the invention particular interest attaches to those that correspond to the formula

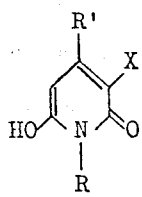

(1)

wherein R and R' each represent a hydrogen atom, an alkyl or aryl radical or a heterocyclic radical and X represents a sulphoalkyl radical.

Of particular interest also are the compounds which are suitable as coupling components and have the formula

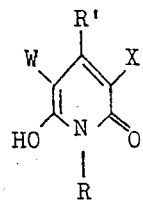

(1a) , wherein R and R' each represent a hydrogen atom, an alkyl or aryl radical or a heterocyclic radical, X represents a sulphoalkyl group and W represents a radical which can be removed in the coupling reaction, whereby a coupling in the 5-position is effected.

As examples of radicals which can be removed in the coupling there may be cited carbonamide, carboxylic acid ester, sulphonamide, sulphonic acid ester, sulphonyl and alkyl- or arylcarbonyl groups. Particularly suitable as removable radicals W are carbonamide radicals.

The sulpho alkyl group which is bound is the 3-position of the pyridone ring is preferably a sulphomethyl group, in particular a group of the formula

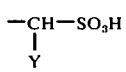

(2) , wherein Y represents a low molecular alkyl radical, an optionally substituted aryl or heterocyclic radical, or preferably a hydrogen atom. Where Y is an aryl radical, this latter may be substituted by alkyl, alkoxy, halogen, acylamino, amino, cyano, nitro or sulphonic acid groups.

Preferred compounds are those of the formulae (1) and (1a) which contain a radical of the formula (2), wherein Y represents a hydrogen atom or a phenyl radical, in particular an aminophenyl or acylaminophenyl radical. Where Y is an aminophenyl radical, the amino group may be subsequently optionally acylated. Important compounds are those that contain on acylaminophenyl radical Y, wherein the acyl group is fibre-reactive. Suitable fibre-reactive groups are in particular halogenotriazinyl groups, and suitable acylating agents are halogenotriazines. Important fibre-reactive compounds of the kind according to the invention are therefore, for example, those of the formula (1), wherein X represents a 3- or 4-(dichloro-1,3,5-triazinylamino)-phenyl-sulpho-methyl group, or a corresponding monochloro-1,3,5-triazinyl compound which, instead of the second chlorine atom, contains the $H_2N$ group of the radical of an amine, alcohol, phenol or mercaptan bound to the triazine nucleus.

The sulphoalkyl-6-hydroxy-pyrid-(2)-ones may exist in several tautomeric forms. In order to simplify the description, the compounds are illustrated in the formulae in only one of these tautomeric forms. It must be expressly stated, however, that the description both here and hereinafter, and particularly in the claims, always refers to compounds in any one of these tautomeric forms.

In particular, the term "pyridone" is intended to include also the compounds in question which are substituted at the nitrogen atom of the pyridone ring by a hydrogen atom, as well as the corresponding 2,6-dihydroxy-pyridines.

The 3-sulphoalkyl-6-hydroxy-pyrid-(2)-ones of the general formula (1) may be substituted in the radicals R and R' by other atoms or groups of atoms, for example by halogen atoms, hydroxy, amino, alkyl, aryl, alkoxy, aryloxy, acylamino, cyano, acyl, carbalkoxy, acyloxy or nitro groups.

A special group of the compounds according to the invention are those of the formula (1), wherein R and R' are hydrogen atoms or alkyl radicals containing at most 4 carbon atoms, especially methyl or ethyl radicals, and X is a sulphomethyl radical, and particularly of the formula (2), wherein Y represents preferably a hydrogen atom.

Another group of compounds according to the invention to which interest attaches for the use described hereinbelow for the manufacture of dyestuffs has the general formula

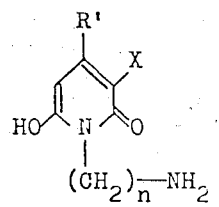

(3)

wherein R' is an alkyl or aryl radical, X is a sulphomethyl group and n is a positive integer, preferably between 1 and 4. Here the important compounds are those in which R' represents a low molecular alkyl radical, in particular a methyl radical.

The 3-sulphoalkyl-6-hydroxy-pyrid-(2)-ones of the formula (1) may be manufactured by reacting unsubstituted pyridones in the 3-position, especially those of the formula

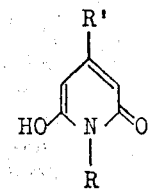 (4) or 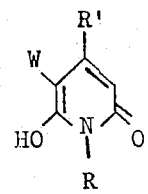 (4a) , wherein R, R' and W have the meanings assigned to them in the elucidation of formulae (1) or (1a), with bisulphite addition compounds of aldehydes, for example in aqueous solution and at normal or elevated temperature. The bisulphite addition compounds of aldehydes which are reacted with the 6-hydroxypyrid-(2)-ones are preferably prepared in advance. However, it is also possible to use them in such a way that they are first formed during the reaction with the 6-hydroxypyrid-(2)-ones. This can be done by adding in small amount an aldehyde to the aqueous mixture of a pyridone with sodium or potassium bisulphite. In order to obtain unitary reaction products of the formula (1), it is advantageous to use as starting materials pyridones which contain in the 5-position of the pyridone ring a removable substituent, for example a —CN, —COOR or —CONH$_2$ group, and to remove this substituent by saponification after the sulphoalkyl group has been introduced.

The compounds according to the invention are new. They are particularly suitable for use as starting compounds for the manufacture of dyestuffs. Thus compounds of the formula (1) in particular can be easily coupled to dyestuffs of the general formula

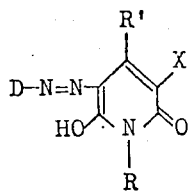

(5)

wherein R, R' and X have the meanings assinged to them hereinbefore and D represents the radical of a diazo component, especially diazo component of the benzene or naphthalene series. Particular importance attaches to dyestuffs of the formula (5) which contain a water-solubilising group, for example a sulphonic acid group, and furthermore contain a reactive radical or a free acylatable amino group, either in the diazo or in the pyridone coupling component, so that the dyestuffs of the formula (5) or the 3-sulphoalkyl-6-hydroxy-pyrid-(2)-one starting compounds such, for example, as those of the formula (3), can be converted into fibre-reactive compounds by acylation with a halide or anhydride of an acyl compound which contains a reactive radical.

A particularly suitable reactive radical is a halogeno-1,3,5-triazine radical.

The dyestuffs of the formula (3) are distinguished by high tinctorial strength. The dyeing obtained with them have brilliant pure yellow shades possessing good fastness properties.

The introduction according to the invention of the sulphonic acid group into the pyridone of the formula (4) offers the advantge that, in water-soluble and compounds which obtain a 1,3,4-trisubstituted 6-hydroxy-pyrid-(2)-one as coupling component, a water-solubilising group is also present in the coupling component in addition to those bound in the diazo component. This feature leads to an improved release of amounts of these dyestuffs which are not fixed on the fibre and to an improved stability of printing pastes which are manufactured from such dyestuffs.

The following Examples illustrate the invention, the parts and percentages being by weight unless otherwise stated and the relationship of parts by weight and parts by volume being the same as that of the gram to the cubic centimetre.

EXAMPLE 1

153 Parts of 1-ethyl-4-methyl-6-hydroxy-pyrid-(2)-one are dissolved at pH 8 in 1500 parts of water with the addition of 100 parts of 40 % sodium hydroxide solution. To this solution is added dropwise at 30°–35° C and within 15 minutes an aqueous solution of the addition compound of sodium bisulphite with formaldehyde (prepared by mixing 260 parts of 40 % sodium bisulphite solution and 81 parts of 77 % formaldehyde solution). The faintly exothermic reaction causes the temperature to rise to 55° C, and the reaction mixture is stirred for 1 hour at this temperature. By means of thin layer chromatography it is possible to detect only a small amount of starting material. The solution is acidified with 110 parts by volume of 36 % hydrochloric acid and cooled to 5° C. After 1 hour a small amunt of crystallised starting material is filtered off. The residual solution whose content of 1-ethyl-3-sulphomethyl-4-methyl-6-hydroxy-pyrid-(1)-one is ascertained by titration with a solution of diazotised aniline and can be used direct for coupling.

If instead of 1-ethyl-4-methyl-6-hydroxy-pyrid-(2)-one there is used 1-phenyl-4-methyl-6-hydroxy-pyrid-(2)-one, 1,4-dimethyl-6-hydroxy-pyrid-(2)-one or 2,6-dihydroxy-4-methylpyridine, the corresponding compounds which contain a sulphomethyl group are obtained likewise according to the directions of this Example.

EXAMPLE 2

A solution of 18.5 parts of cyanuric chloride in 50 parts of acetone in poured into a neutralised solution of 17.3 parts of 1-aminobenzene-3-sulphonic acid nd 100 parts of ice and the pH is maintained at 6 to 7 during the condensation by the dropwise addition of 2N sodium hydroxide solution. Upon completion of the condensation a neutral solution of 1,3-diaminobenzene-4-sulphonic acid is added, the batch warmed to 20°–25° C and the pH of the solution maintained at 6 to 7 by the dropwise addition of 2N and the hydroxide solution. As soon as no further diaminobenzenesulphonic acid can be detected in the mixture, 7 parts of sodium nitrite are added. When the sodium nitrite has completely dissolved the whole solution is poured on a mixture of 200 parts of ice and 25 parts of concentrated hydrochloric acid. The yellow suspension of the diazo compound is stirred for 1 hour in an ice bath, and then a slight excess of nitrous acid is annulled by addition of sulphamic acid. A solution of 24.7 parts of 1-ethyl-3-sulphomethyl-4-methyl-6-hydroxy-pyrid-(2)-one in 160 parts of water is then poured into this diazo suspension. The pH, which initially is 1.5, is raised to 3.5 by the dropwise addition of sodium hydroxide solution, when a clear yellow solution is obtained. This solution is stirred for 1 hour at pH 3.5 in an ice bath, the pH then adjusted to 7 and the dyestuff precipitated by addition of potassium chloride. The resulting dyestuff dyes cotton in pure greenish yellow shades.

EXAMPLE 3

19.6 Parts of 1-ethyl-5-aminocarbonyl-4-methyl-6-hydroxy-pyrid-(2)-one are dissolved in 50 parts of water at pH 7 with the addition of sodium hydroxide solution. To this solution is added a solution of the addition compound of formaldehyde and sodium bisulphite (prepared by mixing 8.1 parts of 37% formaldehyde solution and 26 parts of 40 % sodium bisulphite solution). The reaction mixture is stirred for 1 hour at 80° to 85° C until no more starting material can be detected in it by thin layer chromatography. The mixture is allowed to cool and a distinctly acid reaction to Congo red is produced by addition of 10 ml of 32% hydrochloric acid. The resulting 1-ethyl-3-sulphomethyl-4-methyl-5-aminocarbonyl-6-hydroxy-pyrid-(2)-one is precipitated by addition of 20 parts of potassium chloride. Saponification of the aminocarbonyl group by boiling for 1 hour in 100 parts of 2N sodium hydroxide solution yields the 1-ethyl-3-sulphomethyl-4-methyl-6-hydroxy-pyrid-(2)-one which is identical with the product described in Example 1, paragraph 1.

If instead of 1-ethyl-5-aminocarbonyl-4-methyl-6-hydroxy-pyrid-(2)-one there are used equivalent amounts of 1-phenyl-5-aminocarbonyl-4-methyl-6-hydroxy-pyrid-(2)-one, 1,4-dimethyl-5-aminocarbonyl-6-hydroxy-pyrid-(2)-one, 2,6-dihydroxy-3-aminocarbonyl-4-methylpyridine or 1-butyl-4-phenyl-5-aminocarbonyl-6-hydroxy-pyrid-(2)-one, the corresponding compounds which contain a sulphomethyl group are likewise obtained according to the directions of this Example.

EXAMPLE 4

The process as described in Example 2 is carried out initially. Upon completion of the diazotisation, the diazotisation mixture is adjusted to pH 9 by addition of 20 parts of anhydrous sodium carbonate and a solution of 29 parts of 1-ethyl-3-sulphomethyl-4-methyl-5-aminocarbonyl-6-hydroxypri-(2)-one in 160 parts of water is then added. The coupling is completed after stirring the solution for 2 hours at 10° C. and a pH of approx. 9, accompanied by simultaneous removal of the aminocarbonyl group. The dyestuff is precipitated from the yellow solution by addition of potassium chloride. It is identical with the dyestuff of Example 2.

EXAMPLE 5

To a mixture of 260 parts of 40 % sodium bisulphite solution and 260 parts of ice are added dropwise beneath the surface and within about 15 minutes 44 parts of acetaldehyde and the mixture is stirred until the odour of acetaldehyde has disappeared. The resulting solution is then poured into a solution of 169 parts of 1-(β-hydroxyethyl)-4-methyl-6-hydroxy-pyrid-(2)-one in 500 parts of water and 100 parts of 40 % sodium hydroxide solution. The mixture is stirred for 2 hours at 50–55° C, then cooled to room temperature, made distinctly acid to Congo red by the dropwise addition of concentrated hydrochloric acid and treated with 100 parts of potassium chloride. The 1-(β-hydroxyethyl)-3-(α-sulphoethyl-4-methyl-6-hydroxy-pyrid-(2)-one, which separates out after stirring oversight, is filtered off and dried.

Further pyridines which are substituted in the 3-position by a sulphoalkyl group are obtained by reacting the pyridines listed in column II of the Table below with the bisulphite adducts of the aldehydes listed in column III according to the directions of this Example.

| No. | II Pyridone | III Aldehyde |
|---|---|---|
| 1 | 2,6-Dihydroxy-4-phenyl-pyridine | Acetaldehyde |
| 2 | 1-(4'-Methoxyphenyl)-4-methyl-6-hydroxy-pyrid-(2)-one | Formaldehyde |
| 3 | 1-(β-Chloroethyl)-4-ethyl-6-hydroxy-pyrid-(2)-one | Propionaldehyde |
| 4 | 1-Ethyl-4-butyl-6-hydroxy-pyrid-pyrid-(2)-one | Acetaldehyde |
| 5 | 1-(β-Acetylaminoethyl)-4-methyl-6-hydroxy-pyrid-(2)-one | Formaldehyde |
| 6 | 1-(4'-Toluyl)-4-methyl-6-hydroxy-pyrid-(2)-one | Butyraldehyde |
| 7 | 1-(β-Phenylethyl)-4-methyl-6-hydroxy-pyrid-(2)-one | Formaldehyde |
| 8 | 1-Isopropyl-4-methyl-6-hydroxy-pyrid-(2)-one | Propionaldehyde |
| 9 | 1-Ethyl-4-methyl-6-hydroxy-pyrid-(2)-one | Benzaldehyde |
| 10 | 1-Ethyl-4-methyl-6-hydroxy-pyrid-(2)-one | Benzaldehyde-2-sulphonic acid |
| 11 | " | 4-Acetaminobenzaldehyde |
| 12 | " | 3-Nitrobenzaldehyde |
| 13 | 2,6-Dihydroxy-4-methylpyridine | 2-Chlorobenzaldehyde |
| 14 | 1-Ethyl-4-methyl-6-hydroxy-pyrid-(2)-one | 4-Methoxy-benzaldehyde |
| 15 | " | 3-Sulpho-benzaldehyde |
| 16 | 1-Ethyl-3-aminocarbonyl-4-methyl-6-hydroxy-pyrid-(2)-one | " |
| 17 | 1-Ethyl-4-methyl-6-hydroxy-pyrid-(2)-one | 3-Acetylaminobenzaldehyde |
| 18 | " | 3-Amino-benzaldehyde |
| 19 | 1-Phenyl-4-methyl-6-hydroxy-pyrid-(2)-one | Furfural |
| 20 | 2,6-Dihydroxy-4-methyl-nicotinamide | Thiophene-2-aldehyde |
| 21 | 1-Ethyl-4-methyl-6-hydroxypyrid-(2)-one | Pyridine-3-aldehyde |
| 22 | " | Terephthalaldehyde |

A readily water-soluble yellow reactive dyestuff is obtained by condensing, according to the directions of Example 2, cyanuric chloride with ammonia and subsequently with 1,3-diaminobenzene-4-sulphonic acid, diazotising the resulting product and coupling this with the pyridine of No. 14 of the above Table.

I claim:
1. A compound of the formula

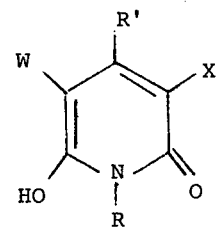

wherein
R and R' may be the same or different, each representing hydrogen; lower alkyl; lower alkyl substituted by hydroxyl, amino, lower alkanoylamino, halo or phenyl; phenyl; or pheyl substituted by lower alkyl or lower alkoxy;
W is hydrogen or $H_2NCO-$, and
X is

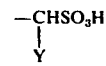

wherein
Y is hydrogen; lower alkyl; phenyl; phenyl substituted by nitro, halo, lower alkoxy, amino, lower alkanoylamino, sulfo or carboxyl; furyl; thiofuryl; or pyridyl.

2. A compound according to claim 1, wherein W represents the carboxamide group.

3. A compound of claim 1 wherein R and R' are hydrogen or alkyl of 1 to 4 carbon atoms.

4. A compound of claim 1 wherein R and R' are hydrogen, methyl or ethyl.

5. A compound of claim 1 wherein R is —(CH$_2$)$_n$—NH$_2$, wherein n is 1 to 4.

6. A compound of claim 5, wherein R' is lower alkyl.

7. A compound of claim 6, wherein R' is methyl.

8. A compound according to claim 1 of the formula

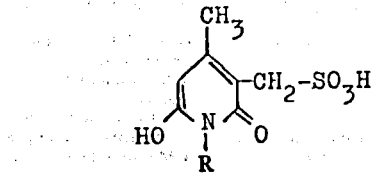

wherein R is a low molecular alkyl radical.

9. The compound according to claim 8 of the formula

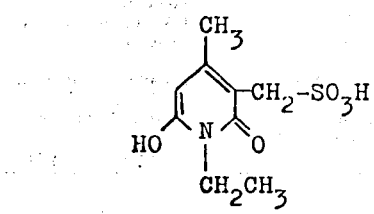

10. A compound according to claim 1 of the formula

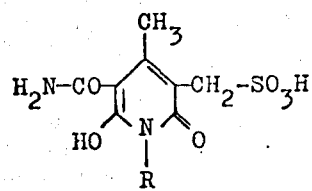

wherein R is a low molecular alkyl radical.

11. The compound according to claim 10 of the formula

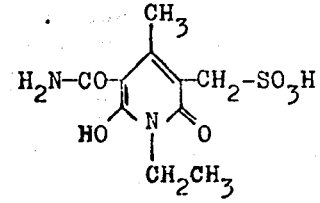

* * * * *